US00PP12278P2

(12) United States Plant Patent
Drewlow

(10) Patent No.: US PP12,278 P2
(45) Date of Patent: Dec. 11, 2001

(54) NEW GUINEA IMPATIENS PLANT NAMED 'OVATION LAVENDER'

(75) Inventor: Lyndon W. Drewlow, County of Santa Barbara, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,510

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Lavender, characterized by its lavender flower color, large flower diameter, dark green leaves, early flowering, long-lasting flowering, self-branching and vigorous habit.

1 Drawing Sheet

The present invention relates to a new and distinctive cultivar of Impatiens plant, botanically known as *Impatiens Hawkeri*, commercially known as New Guinea Impatiens, and known by the cultivar name 'Ovation Lavender'. Ovation Lavender was developed in a controlled breeding program by crossing Mikkelsen Seedling No. 94-546-1 (seed parent) with Mikkelsen Seedling No. 95- 1116-4 (pollen parent). Both parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry:

1. Ovation Lavender has Purple Group 75A flower color while Celebration Light Lavender Improved (patent pending) has Violet Group 87C flower color and Toga (U.S. Plant Pat. No. 10,304) has flowers colored Purple-Violet Group 82C.
2. Ovation Lavender has larger flowers at 7.0 to 7.5 cm than Celebration Light Lavender Improved at 6 to 6.5 cm in diameter. Ovation Lavender Flowers are similar in size to Toga.
3. Ovation Lavender has dark green leaves with a red-purple cast while Toga has deep green leaves and Celebration Light Lavender Improved has light green leaves.
4. Ovation Lavender has a mounded growth habit while Celebration Light Lavender Improved and Toga have a more upright growth habit.
5. Ovation Lavender is intermediate in height with Toga being more compact and Celebration Light Lavender Improved being taller.
6. Ovation Lavender has the smallest leaves with the average mature leaf being 8 to 9 cm long while Toga has 10 to 11 cm long leaves and Celebration Light Lavender Improved leaves are 12 to 13 cm long.
7. Ovation Lavender has yellow-green spurs while Celebration Light Lavender Improved has yellow-green spurs with a red-purple cast and Toga has red-purple spurs.

8. Ovation Lavender has yellow-green pedicels which is similar to Celebration Light Lavender Improved while Toga has red-purple pedicels.
9. Ovation Lavender has red-purple leaf midribs while Toga has red-purple midrib coloration on lower part of leaf and Celebration Light Lavender Improved has light green midribs.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional trace elements added. Habit of growth, foliage coloration, leaf variegation, size of leaves, and flower size will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 94-546-1 and male parent Mikkelsen Seedling No. 95-1116-4.

Propagation:

(*A*) *Type cutting*.—Stem tip 15 mm long will develop to 4 to 5 cm long in 18 to 21 days.

(*B*) *Time to root*.—8–10 days at 23° C. summer; 10–12 days at 20° C. winter.

(*C*) *Rooting habit*.—Heavy, fiborous.

Plant description:

(*A*) *Form and habit of growth*.—Mounded, self-branched, intermediate in height, flowers open over the top of leaf canopy; continuous flowering; vigorous growing flowering herb. Average height is 21 to 25 cm and average width is 45 to 50 cm. Internode length is 6 to 7 cm but is highly variable. Pedicel is Yellow-Green Group 146D, stem is Yellow-Green Group 147C with a Greyed-Purple Group 185B cast, and node is Greyed-Purple Group 185B. Pedicel length is 4 cm.

(*B*) *Foliage description*.—Dark green with red-purple cast, red-purple midrib, and no leaf variegation. (1) Size: 8 to 9 cm long and 3 to 3.5 cm wide on average mature leaf. (2) Shape: Lanceolate with acuminate apex and acute base. (3) Texture: Both upper and lower surfaces are glabrous. (4) Margin: Entire with fine cilia. (5) Color: Young foliage, top side is Yellow-Green Group 147A with Greyed-Purple Group 183A cast, underside is Greyed-Purple Group 183A. Mature foliage, top side is Yellow-Green Group 147A with Greyed-Purple Group 183A cast, underside is Greyed-Purple Group 183A. (6) Venation: Pinnate, upper side is Greyed-Purple Group 184C and lower side is Greyed-Purple Group 184B. (7) Young midrib is Greyed-Purple Group 185A and mature midrib is Greyed-Purple Group 185B.

(*C*) *Branching*.—The branching is naturally occurring. Lateral branching at base: 5 or more lateral branches. Lateral branch length is 15 to 18 cm but is highly variable.

Flowering description:

(*A*) *Flowering habits*.—Flowers continuously from leaf whorl in a progressively orderly manner with one flower per leaf axil. When the last flower in a whorl opens the first flower in the whorl above starts to open. It takes 5 to 7 days for a mature bud to fully open and the flower may last two weeks or longer depending on the environment. The time to first flower is approximately 8 weeks from root cuttings. The flowers are self-cleaning.

(*B*) *Natural flowering season*.—Indeterminant and continuous; quantity of flowering increases with increasing levels of light.

(*C*) *Flower bud*.—Ellipsoidal; flowers perfect; spur color is light green with deep green tip that is 4.0 cm long on mature bud, with the throat behind the ovary and originating from the major sepal. Bud length is 18 to 20 mm and bud diameter is 16 mm. Spur is Yellow-Green Group 146D, spur tip is Yellow-Green Group 146B, and flower bud is Purple-Violet Group 80B.

(*D*) *Flowers borne*.—On individual yellow-green pedicels 4.0 cm long from a whorl of usually five leaves. Flowering progressively around the whorls as buds and leaves develop. Leaf axils have one flower each.

(*E*) *Quantity of flowers*.—Numerous because of self-branching nature of plant and the long-lasting flower characteristic.

(*F*) *Diameter of flower*.—7.0 to 7.5 cm. Flower Depth: 5 mm.

(*G*) *Petals*.—(1) Shape: Heart, keel petals are largest. (2) Color: Top side in winter when opening is Purple Group 75A, deepening only in center of standard petal to Red-Purple Group 67C; underside is Purple Group 77C with Red-Purple Group 67C at center on each petal that divides the two lobes. (3) Number of petals: Five. (4) Size of petals: Standard: 4.5 cm wide and 3.0 cm long, equal lobes with shallow cut. Wings: 3.5 cm wide and 3.5 cm long, unequal lobes with moderate cut. Keel: 4.0 cm wide and 3.5 cm long, unequal lobes with moderate cut.

(*H*) *Reproductive organs*.—(1) Stamens: Five in number. (a) Anther: Hooded shape, color is Yellow-White Group 158B with a Purple-Violet Group 81C cast. (b) Pollen color: Yellow-White Group 158C. (2) Pistils: (a) Stigma: Five, segmented column, is Red-Purple Group 64C color. (b) Style color: Red-purple. (c) Ovaries: Five in number, size is 8 mm when immature, color is Greyed-Purple Group 185A.

(*I*) *Fertility*.—The plants are fertile, but do not normally set seed under greenhouse or garden conditions, unless in a controlled crossing program.

Disease resistance: No significant disease or insect problems seen to date.

OTHER IMPORTANT CHARACTERISTICS

1. Self-branching, early flowering nature allows cultivar to be grown in 10 cm pots but is also vigorous enough to be grown in 15 to 25 cm containers as well.

2. Minimal fading of older flowers; large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Lavender, as illustrated and described.

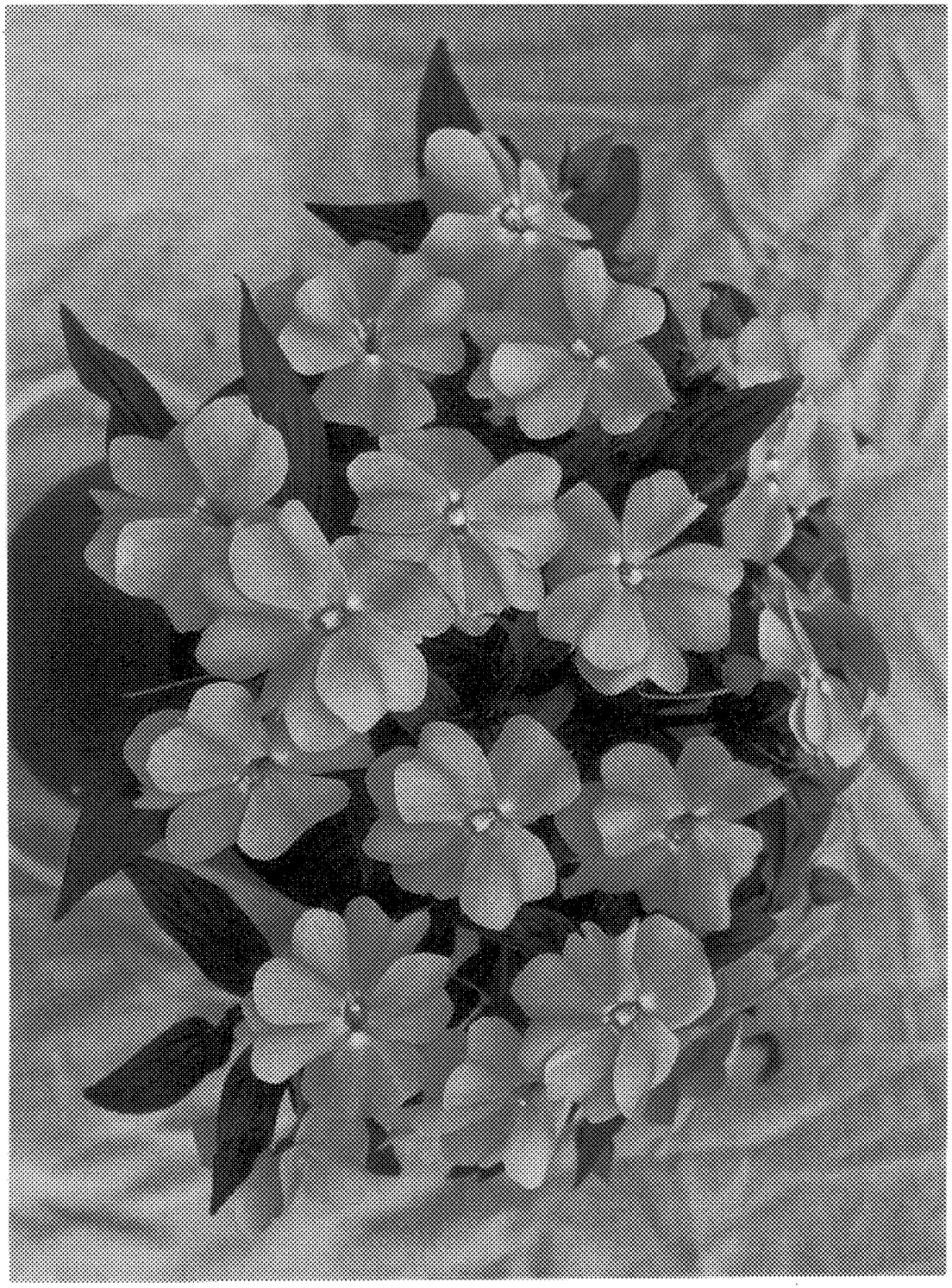

* * * * *